US006521225B1

(12) United States Patent
Srivastava et al.

(10) Patent No.: US 6,521,225 B1
(45) Date of Patent: Feb. 18, 2003

(54) AAV VECTORS

(75) Inventors: Arun Srivastava, Indianapolis, IN (US); Selvarangan Ponnazhagan, Cleveland, OH (US); Robert H. Chloemer, Indianapolis, IN (US); Xu-Shan Wang, Carmel, IN (US); Mervin C. Yoder, Indianapolis, IN (US); Shang-Zhen Zhou, Alameda, CA (US); Jaime Escobedo, Alamo, CA (US); Varavani Dwarki, Alameda, CA (US)

(73) Assignees: Chiron Corporation, Emeryville, CA (US); Advanced Research and Technology Institute, Bloomington, IN (US)

( * ) Notice: Subject to any disclaimer, the term of this patent is extended or adjusted under 35 U.S.C. 154(b) by 0 days.

(21) Appl. No.: 08/921,497

(22) Filed: Sep. 2, 1997

Related U.S. Application Data

(60) Provisional application No. 60/025,616, filed on Sep. 6, 1996, and provisional application No. 60/025,649, filed on Sep. 11, 1996.

(51) Int. Cl.$^7$ ............................................. A61K 35/00

(52) U.S. Cl. .................................... 424/93.2; 424/93.1

(58) Field of Search ........................ 514/44; 536/23.1; 435/320.1, 172.3; 935/23; 424/93.2, 93.1

(56) References Cited

U.S. PATENT DOCUMENTS

| | | | |
|---|---|---|---|
| 5,252,479 A | | 10/1993 | Srivastava |
| 5,436,146 A | * | 7/1995 | Shenk et al. ............. 435/172.3 |
| 5,780,447 A | * | 7/1998 | Nienhuis ..................... 514/44 |
| 5,972,899 A | * | 10/1999 | Zychlinsky et al. .......... 514/44 |

FOREIGN PATENT DOCUMENTS

| | | | | |
|---|---|---|---|---|
| WO | WO 93/09239 | * | 5/1993 | ........... C12N/15/86 |
| WO | WO 94/28157 | * | 12/1994 | ........... C12P/21/06 |

OTHER PUBLICATIONS

Friedmann, T. et al. Overcoming the obstacle to gene therapy. Scientific American, p. 96–101, Jun. 1997.*

Verma, I. et al. Gene therapy–promises, problems and prospects. Nature, vol. 389, pp. 239–242, Sep. 18, 1997.*

Herz, J. and Gerard, R.D. Adenovirus–mediated transfer of low density lipoprotein receptor gene acutely accelerates cholesterol clearance in ormal mice. Proc. Natl. Acad. Sci. USA. pp. 2812–2816, Apr. 1993.*

Su, H. et al. Selective killing of AFP–positive hepatocellular carcinoma cells by adeno–associated virus transfer of the herpes simplex virus thymidine kinase gene. Hum Gene Therapy p. 463–70, May 1, 1996.*

Orkin S. and Motulsky, A. Report and recommendations of the panel to assess the NIH investment in research on gene therapy. NIH report. all pages, Dec. 7, 1995.*

Eck and Wilson, Goodman and Gilman's The Pharmacological Basis of Therapeutics, 9th Ed. p77–101, 1995.*

Fisher, et al., "*Transduction with Recombinant Adeno–Associated Virus for Gene Theraphy Is Limited by Leading–Strand Synthesis,*" Journal of Virology, 70(1):520–532 (Jan. 1996).

Flotte,et al., "*An improved system for packaging recombinant adeno–associated virus vectors capable of in vivo transduction*",Gene Therapy 2:29–37 (1995).

Koeberl, et al., "Persistent expression of human clotting factor IX from mouse liver after intravenous injection of adeno–associated virus vectors," *Proc. Natl. Acad. Sci. U.S.A.* 94, 1426–1431 (Feb. 1997).

Ponnazhagan, et al., "Adeno–associated virus 2–mediated gene trasfer in vivo: organ–tropism and expression of transduced saquences in mice," *Gene* 190:203–210 (1997).

Koberl, et al., "Transduction of hepatocytes in vivo with adeno–associated virus vectors as a model for hepatic gene therapy,"*American Journal of Human Genetics* , 57(4):A43, abstract No. 218 (Oct. 24, 1995).

Ponnazhagan et al., "Adeno–associated virus 2–mediated gene transfer an expression in murine hematopoietic progenitor cells in vivo." *Blood*, 10(1): 240a, Abstract No. 948 (Dec., 1995).

Ponnazhagan, et al., "Differential expression of human cells from the p6 promoter of human parovirus B19 following plasmid tranfection and recombinant adeno–associated virus 2 (AAV) infection: human megakaryocytic leukaemia cells are non–permissive for AAV infection," *Journal of General Virology* , 77:1111–1122 (Jun., 1996).

Sokol, et al., "*Human genome–chromosome No. 19. Casopis Lekaru Ceskvch,*"Database on Medline, Abstract No. 96074978, *134(19)* ,625–629 (Oct., 1995).

Wang, et al., "Rescue and replication signals of the adeno–associated virus 2 genome," *Journal of Molecular Biology* , 250:5730–580 (1995).

Wang, et al., "Rescue and replication of adeno–associated virus type 2 as well as vector DNA sequences from recombinant plasmids containing deletions in the viral inverted terminal repeats:Selective encapsidation of viral genomes in progeny virions," *Journal of Virology, 70(3):* 1668–1677 (Mar., 1996).

Written Opinion PCT/US97/15453, International Preliminary Examining Authority Jul. 24, 1998.

* cited by examiner

Primary Examiner—Michael C. Wilson
(74) Attorney, Agent, or Firm—Donald Pochopien; Alisa A. Harbin; Robert P. Blackburn

(57) ABSTRACT

The present invention is directed to a recombinant adenovirus vector comprising two inverted terminal repeats (ITRs) each of which comprises a D-sequence having (i) from 5 to 15 native nucleotides and (ii) one or more deletions or substitutions therein.

6 Claims, 4 Drawing Sheets

SEQUENCE LISTING

```
<160> NUMBER OF SEQ ID NOS: 26

<210> SEQ ID NO 1
<211> LENGTH: 19
<212> TYPE: DNA
<213> ORGANISM: Artificial Sequence
<220> FEATURE:
<223> OTHER INFORMATION: The full sequence for lacZ from plasmid PCMV
      p-lacZ  is found in Ponnazhagan, et al., J. Gen Virol.,
      77:1111-1122 (1996)
<221> NAME/KEY: misc_feature
<223> OTHER INFORMATION: primer for lacZ

<400> SEQUENCE: 1
gatgagcgtg gtggttatg                                                    19

<210> SEQ ID NO 2
<211> LENGTH: 19
<212> TYPE: DNA
<213> ORGANISM: Artificial Sequence
<220> FEATURE:
<223> OTHER INFORMATION: The full sequence for lacZ from plasmid PCMV
      p-lacZ  is found in Ponnazhagan, et al., J. Gen Virol.,
      77:1111-1122 (1996)
<221> NAME/KEY: misc_feature
<223> OTHER INFORMATION: primer for lacZ

<400> SEQUENCE: 2
tacagcgcgt cgtgattag                                                    19

<210> SEQ ID NO 3
<211> LENGTH: 20
<212> TYPE: DNA
<213> ORGANISM: homo sapiens
<220> FEATURE:
<221> NAME/KEY: misc_feature
<223> OTHER INFORMATION: primer for human beta-globin promoter

<400> SEQUENCE: 3
gatggtatgg ggccaagaga                                                   20

<210> SEQ ID NO 4
<211> LENGTH: 20
<212> TYPE: DNA
<213> ORGANISM: homo sapiens
<220> FEATURE:
<221> NAME/KEY: misc_feature
<223> OTHER INFORMATION: primer for human gamma-globin

<400> SEQUENCE: 4
```
gggtttctcc tccagcatct                                                  20

<210> SEQ ID NO 5
<211> LENGTH: 20
<212> TYPE: DNA
<213> ORGANISM: mouse
<220> FEATURE:
<221> NAME/KEY: misc_feature
<223> OTHER INFORMATION: primer for the mouse beta-actin gene

<400> SEQUENCE: 5
accttcaaca ccccagccat                                                  20

<210> SEQ ID NO 6
<211> LENGTH: 20
<212> TYPE: DNA
<213> ORGANISM: mouse
<220> FEATURE:
<221> NAME/KEY: misc_feature
<223> OTHER INFORMATION: primer for the mouse beta-actin gene

<400> SEQUENCE: 6
tcaggcagct catagctctt                                                  20

<210> SEQ ID NO 7
<211> LENGTH: 20
<212> TYPE: DNA
<213> ORGANISM: adenoassociated virus
<220> FEATURE:
<221> NAME/KEY: misc_feature
<223> OTHER INFORMATION: D-sequence in ITRs

<400> SEQUENCE: 7
ctccatcact aggggttcct                                                  20

<210> SEQ ID NO 8
<211> LENGTH: 20
<212> TYPE: DNA
<213> ORGANISM: adenoassociated virus
<220> FEATURE:
<221> NAME/KEY: misc_feature
<223> OTHER INFORMATION: D-sequence in ITRs
      Antisense strand

<400> SEQUENCE: 8
aggaacccct agtgatggag                                                  20

<210> SEQ ID NO 9
<211> LENGTH: 21
<212> TYPE: DNA
<213> ORGANISM: adenoassociated virus
<220> FEATURE:
<221> NAME/KEY: misc_feature
<223> OTHER INFORMATION: substitute D-sequence in ITRs

<400> SEQUENCE: 9
ccaatattag atctgatatc a                                                21

<210> SEQ ID NO 10
<211> LENGTH: 25
<212> TYPE: DNA
<213> ORGANISM: adenoassociated virus
<220> FEATURE:
<221> NAME/KEY: misc_feature
<223> OTHER INFORMATION: substitute D-sequence in ITRs
      Antisense strand

<400> SEQUENCE: 10

```
ctagtgatat cagatctaat attgg                                              25

<210> SEQ ID NO 11
<211> LENGTH: 24
<212> TYPE: DNA
<213> ORGANISM: adenoassociated virus
<220> FEATURE:
<221> NAME/KEY: misc_feature
<223> OTHER INFORMATION: D-sequence in ITRs

<400> SEQUENCE: 11
ccaactccag atctgatatc actt                                               24

<210> SEQ ID NO 12
<211> LENGTH: 5
<212> TYPE: DNA
<213> ORGANISM: adenoassociated virus
<220> FEATURE:
<221> NAME/KEY: misc_feature
<223> OTHER INFORMATION: D-sequence in ITRs

<400> SEQUENCE: 12 ctcca                                                                     5

<210> SEQ ID NO 13
<211> LENGTH: 28
<212> TYPE: DNA
<213> ORGANISM: adenoassociated virus
<220> FEATURE:
<221> NAME/KEY: misc_feature
<223> OTHER INFORMATION: D-sequence in ITRs
      Antisense strand

<400> SEQUENCE: 13
ctagaagtga tatcagatct ggagttgg                                           28

<210> SEQ ID NO 14
<211> LENGTH: 5
<212> TYPE: DNA
<213> ORGANISM: adenoassociated virus
<220> FEATURE:
<221> NAME/KEY: misc_feature
<223> OTHER INFORMATION: D-sequence in ITRs
      Antisense strand

<400> SEQUENCE: 14 tggag                                                                     5

<210> SEQ ID NO 15
<211> LENGTH: 24
<212> TYPE: DNA
<213> ORGANISM: adenoassociated virus
<220> FEATURE:
<221> NAME/KEY: misc_feature
<223> OTHER INFORMATION: D-sequence in ITRs

<400> SEQUENCE: 15
ccaactccat cactgatatc actt                                               24

<210> SEQ ID NO 16
<211> LENGTH: 10
<212> TYPE: DNA
<213> ORGANISM: adenoassociated virus
<220> FEATURE:
<221> NAME/KEY: misc_feature
<223> OTHER INFORMATION: D-sequence in ITRs
```

```
<400> SEQUENCE: 16
ctccatcact                                                              10

<210> SEQ ID NO 17
<211> LENGTH: 28
<212> TYPE: DNA
<213> ORGANISM: adenoassociated virus
<220> FEATURE:
<221> NAME/KEY: misc_feature
<223> OTHER INFORMATION: D-sequence in ITRs
      Antisense strand

<400> SEQUENCE: 17
ctagaagtga tatcagtgat ggagttgg                                          28

<210> SEQ ID NO 18
<211> LENGTH: 10
<212> TYPE: DNA
<213> ORGANISM: adenoassociated virus
<220> FEATURE:
<221> NAME/KEY: misc_feature
<223> OTHER INFORMATION: D-sequence in ITRs
      Antisense strand

<400> SEQUENCE: 18
agtgatggag                                                              10

<210> SEQ ID NO 19
<211> LENGTH: 24
<212> TYPE: DNA
<213> ORGANISM: adenoassociated virus
<220> FEATURE:
<221> NAME/KEY: misc_feature
<223> OTHER INFORMATION: D-sequence in ITRs

<400> SEQUENCE: 19
ccaactccat cactaggggc actt                                              24

<210> SEQ ID NO 20
<211> LENGTH: 15
<212> TYPE: DNA
<213> ORGANISM: adenoassociated virus
<220> FEATURE:
<221> NAME/KEY: misc_feature
<223> OTHER INFORMATION: D-sequence in ITRs

<400> SEQUENCE: 20
ctccatcact agggg                                                        15

<210> SEQ ID NO 21
<211> LENGTH: 28
<212> TYPE: DNA
<213> ORGANISM: adenoassociated virus
<220> FEATURE:
<221> NAME/KEY: misc_feature
<223> OTHER INFORMATION: D-sequence in ITRs
      Antisense strand

<400> SEQUENCE: 21
ctagaagtgc ccctagtgat ggagttgg                                          28

<210> SEQ ID NO 22
<211> LENGTH: 15
<212> TYPE: DNA
<213> ORGANISM: adenoassociated virus
<220> FEATURE:
<221> NAME/KEY: misc_feature
```

```
<223> OTHER INFORMATION: D-sequence in ITRs
      Antisense strand

<400> SEQUENCE: 22
cccctagtga tggag                                                        15

<210> SEQ ID NO 23
<211> LENGTH: 24
<212> TYPE: DNA
<213> ORGANISM: adenoassociated virus
<220> FEATURE:
<221> NAME/KEY: misc_feature
<223> OTHER INFORMATION: D-sequence in ITRs

<400> SEQUENCE: 23
ccaactccat cactagggt tcct                                               24

<210> SEQ ID NO 24
<211> LENGTH: 20
<212> TYPE: DNA
<213> ORGANISM: adenoassociated virus
<220> FEATURE:
<221> NAME/KEY: misc_feature
<223> OTHER INFORMATION: D-sequence in ITRs

<400> SEQUENCE: 24
ctccatcact aggggttcct                                                   20

<210> SEQ ID NO 25
<211> LENGTH: 28
<212> TYPE: DNA
<213> ORGANISM: adenoassociated virus
<220> FEATURE:
<221> NAME/KEY: misc_feature
<223> OTHER INFORMATION: D-sequence in ITRs
      Antisense strand

<400> SEQUENCE: 25
ctagaggaac ccctagtgat ggagttgg                                          28

<210> SEQ ID NO 26
<211> LENGTH: 20
<212> TYPE: DNA
<213> ORGANISM: adenoassociated virus
<220> FEATURE:
<221> NAME/KEY: misc_feature
<223> OTHER INFORMATION: D-sequence in ITRs
      Antisense strand

<400> SEQUENCE: 26
aggaacccct agtgatggag                                                   20
```

AAV VECTORS

Provisional Application No. 60/025,616 Sep. 6, 1996, No. 60/025,649 Sep. 11, 1996.

BACKGROUND

The therapeutic treatment of diseases and disorders by gene therapy involves the transfer and stable insertion of new genetic information into cells. Although a variety of physical and chemical methods have been developed for introducing exogenous DNA into eukaryotic cells, viruses have generally been proven to be more efficient for this purpose. Several DNA-containing viruses, such as parvoviruses, adenoviruses and herpesviruses, and RNA-containing viruses, such as retroviruses, have been used to construct eukaryotic cloning and expression vectors and explored as gene therapy vehicles.

Retrovirus- and adenovirus-based vectors are associated with certain complications and disadvantages. For example, retroviruses are intimately associated with neoplastic events. See Donahue, Helper virus induced T cell lymphoma in non-human primates after retroviral mediated gene transfer, *J. Exp. Med.* 176 (1992) 1125–1135. Adenovirus induces a CTL response. See Yang, MHC class 1-restricted cytotoxic T lymphocytes to viral antigens destroy hepatocytes in mice infected with E1-deleted recombinant adenoviruses, *Immunity* 1 (1994) 433–442. It also requires a relatively large (35 kb) viral genome, making its usefulness as a vehicle to deliver large sequences limited.

Thus, an alternative vector which is neither pathogenic nor immunogenic would be advantageous. In contrast to adenoviruses, the parvovirus, adeno-associated virus (AAV), has a much smaller genome, most of which can be replaced by foreign DNA. Parvoviruses are small, icohedral viruses approximately 25 nm in diameter containing a single strand DNA genome of approximately 5 kilobases (kb). They consist of two major classes: the dependoviruses, including AAV and its subtypes (AAV1, AAV2, AAV3, AAV4 and AAV5), and the autonomous parvoviruses. The latter lytically infect permissive, proliferating cells in nonintegrating manner without helper virus assistance. On the other hand, AAV is a non-pathogenic human parvovirus that requires co-infection with a helper virus, usually adenovirus (or herpesvirus), for its optimal replication. See for example, Berns, Parvovirus replication, *Microbiol. Rev.* 54 (1990) 316–329 and Berns and Bohenzky, Adeno-associated viruses: an update, *Adv. Virus Res.* 32 (1987) 243–306.

In the absence of a helper virus, the wild-type (wt) AAV has been shown to integrate into the human chromosome 19 in a site-specific manner. See Kotin and Berns, Organization of adeno-associated virus DNA in latently infected Detroit 6 cells, *Virol.* 170 (1989) 460–467; Kotin, Mapping and direct visualization of a region-specific viral DNA integration site on chromosome 19q13-qter, *Genomics* 10 (1991) 831–834; Kotin, Site-specific integration by adeno-associated virus, *Proc. Natl. Acad. Sci.* 87 (1990) 2211–2215 and Samulski, Targeted integration of adeno-associated virus (AAV) into human chromosome 19, *EMBO J.* 10 (1991) 3941–3950. Recombinant AAV vectors appear to lack this site-specificity of integration. See Ponnazhagan, Adeno-associated virus 2-mediated transduction of murine hematopoietic cells and long-term expression of a human globin gene in vivo, 6th *Parvovirus Workshop*, Montpellier, France. p29, (1995). Nevertheless, it has been suggested that the AAV-based vector system may prove to be a safer alternative to the more commonly used retrovirus- and adenovirus-based vectors. See, for example, Muzyczka, Use of adeno-associated virus as a general transduction vector for mammalian cells, *Curr. Top. Microbiol. Immunol.* 158 (1992) 97–129. Because approximately 90% of the human population is sero-positive for AAV (see, for example, Blacklow, A sero-epidemiologic study of adeno-associated virus infection in infants and children, *Am. J. Epidemiol.* 94 (1971) 359–366), accidental infection by recombinant AAV is not likely to be problematic. Furthermore, relatively higher stability, higher titers, and higher transduction efficiency of AAV have added to the desirable features of AAV vectors. See Carter, Adeno-associated virus vectors, *Curr. Opin. Biotechnol.* 3 (1993) 533–538 and Srivastava, Parvovirus-based vectors for human gene therapy, *Blood Cells* 20 (1994) 531–538.

A number of studies have reported AAV-mediated successful transduction and expression of therapeutic genes in vitro. For example, see Chatterjee, Dual target inhibition of HIV-1 in vitro by means of an adeno-associated virus antisense vector, *Science* 258 (1992) 1485–1488; Walsh, Regulated high level expression of a human γ-globin gene introduced into erythroid cells by an adeno-associated virus vector, *Proc. Natl. Acad. Sci.* 89 (1992) 7257–7261; Walsh, Phenotypic correction of Fanconi anemia in human hematopoietic cells with a recombinant adeno-associated virus vector, *J. Clin. Invest.* 94 (1994) 1440–1448; Flotte, Expression of the cystic fibrosis transmembrane conductance regulator from a novel adeno-associated virus promoter, *J. Biol. Chem.* 268 (1993) 3781–3790; Ponnazhagan, Suppression of human α-globin gene expression mediated by the recombinant adeno-associated virus 2-based antisense vectors, *J. Exp. Med.* 179 (1994) 733–738; Miller, Recombinant adeno-associated virus (rAAV)-mediated expression of human γ-globin gene in human progenitor-derived erythroid cells, *Proc. Natl. Acad. Sci.* 91 (1994) 10183–10187; Einerhand, Regulated high-level human beta-globin gene expression in erythroid cells following recombinant adeno-associated virus-mediated gene transfer, *Gene Ther.* 2 (1995) 336–343; Luo, Adeno-associated virus 2-mediated gene transfer and functional expression of the human granulocyte-macrophage colony-stimulating factor, *Exp. Hematol.* 23 (1995) 1261–1267; and Zhou, Adeno-associated virus 2-mediated transduction and erythroid cell-specific expression of a human β-globin gene, *Gene Therapy* 3 (1996) 223–229.

A few studies have examined the safety and efficacy of the AAV vectors in vivo (see Flotte, Stable in vivo expression of the cystic fibrosis transmembrane conductance regulator with an adeno-associated virus vector, *Proc. Natl. Acad. Sci.* 90 (1993) 10613–10617 and Kaplitt, Long-term gene expression and phenotypic correction using adeno-associated virus vectors in the mammalian brain, *Nature Genet.* 8 (1994) 148–153).

A disadvantage of AAV vectors in some clinical indications is the generalized nature of AAV infection. Previous studies have indicated that AAV possesses a wide host range that transcends the species barrier. See for example Muzyczka, Use of adeno-associated virus as a general transduction vector for mammalian cells, *Curr. Top. Microbiol. Immunol.* 158 (1992) 97–129. The autonomous parvovirus, LuIII, appears to possess a similarly wide host range, since liver specific expression has been obtained only via use of recombinants containing a liver-specific enhancer and a regulated promoter. See Maxwell, Autonomous parvovirus transduction of a gene under control of tissue-specific or inducible promoters, *Gene Therapy* 3 (1996) 28036. Surprisingly, we have discovered that AAV exhibits organ tropism for the liver and is therefore uniquely adapted for the treatment of diseases or conditions of the liver, diseases or conditions characterized by involving a protein made in the liver or diseases or conditions in which systemic administration of a therapeutic via the liver is desirable or advantageous.

INVENTION SUMMARY

In one aspect, the invention provides methods for selectively expressing therapeutic molecules, such as secretory proteins, antisense molecules and ribozymes, in the liver. The methods find use in treating hepatic diseases or conditions. The methods also find use in treating any disease or condition in which systemic administration of the therapeutic substance, for example a secretory protein, is desired. The methods also find use in treating or diseases or conditions involving proteins that originate or are normally made in the liver.

The methods involve administering to a mammalian patient having a need for liver expression of a therapeutic molecule a therapeutically effective amount of an AAV vector containing a the therapeutic molecule. The AAV vectors are administered by intravenous injection, such as by intraportal vein injection. Therapeutic molecules useful in treating hepatic diseases or conditions which can be administered employing the methods described here include, for example, insulin and thymidine kinase. Therapeutic molecules comprising proteins originating in the liver or protein normally made in the liver include, for example, the LDL receptor, Factor VIII, Factor IX, phenylalanine hydroxylase (PAH), omithine transcarbamylase (OTC), and α1-antitrypsin. Therapeutic molecules comprising secretory proteins in which systemic administration is advantageously attained via liver specific delivery include, for example, cytokines, growth factors and the colony stimulating factors, G-CSF and GM-CSF. Additional protein therapeutic molecules contemplated for use in the methods and compositions of the invention are described infra.

Also included are nucleic acid sequences that encode antisense molecules that are useful in treating a hepatic disease. The antisense molecule will be an RNA sequence that can prevent or limit the expression of over-produced, defective, or otherwise undesirable molecules by being sufficiently complementary in sequence to the target sequence that it binds to the target sequence. For example, the target sequence can be part of the mRNA that encodes a protein, and the antisense RNA would bind to the mRNA and prevent translation. The target sequence can be part of a gene that is essential for transcription, and the antisense RNA would bind to the gene segment and prevent or limit transcription. For example, Group C adenoviruses Ad2 and Ad5 have a 19 kiloDalton glycoprotein (gp 19) encoded in the E3 region of the virus that binds to class I MHC molecules in the endoplasmic reticulum of cells and prevents terminal glycosylation and translation of the molecule to the cell surface. Prior to liver transplantation, the liver cells may be infected with gp 19-encoding AAV vectors or virions which upon expression of the gp 19 inhibit the surface expression of class I MHC transplantation antigens. These donor cells may be transplanted with low risk of graft rejection and may require a minimal immunosuppressive regimen for the patient. It may also permit a donor-recipient state to exist with fewer complications.

Similar treatments may be used to treat chronic hepatitis B infections or non-A non-B hepatitis. The vector can be engineered to include a structural hepatitis gene, polyadenylation signal or a fragment thereof in reverse orientation such that the expression product binds to hepatitis virus mRNA transcripts, preventing translation of the structural protein and ultimately "inactivating" the virus. See, for example, Wu, Specific inhibition of hepatitis B viral gene expression in vitro by targeted antisense oligonucleotides, *J. Biol. Chem.* 267 (1992) 12436–12439 and Offensperger, In vivo inhibition of duck hepatitis B virus replication and gene expression by phosphorothioate modified antisense oligodeoxynyucleotides, *EMBO J.* 12 (1993) 1257–1262.

Also included are nucleic acid sequences that encode ribozymes that are useful in treating various diseases and conditions. Ribozymes are RNA polynucleotides capable of catalyzing RNA cleavage at a specific sequence and hence useful for attacking particular mRNA molecules. In chronic myelogenous leukemia for example, the "Philadelphia chromosomal translocation" causes expression of a bcr-abl fusion protein and abnormal function of the abl oncoprotein. Because the fusion mRNA occurs only in cells that have undergone the chromosome translocation and because the fusion transcript contains only two possible sequences at the splice junction, a ribozyme specific for either of the two bcr-abl fusion mRNA splice junctions can inhibit expression of the oncoprotein. Exemplary ribozymes include ribozymes to hepatitis A, hepatitis B and hepatitis C. See Christoffersen and Marr, *J. Med. Chem.* 38 (1995) 2023–2037 and Barpolome, *J. Hepatol.* 22 (1995) 57–64.

Currently preferred therapeutic molecules are the LDL receptor, Factor VIII, Factor IX, PAH, TPO (thrombopoietin) and EPO (erythropoietin). Also preferred are growth factors and cytokines. A therapeutically effective amount of the therapeutic molecule for purposes of this invention is at least about $10^9$ to about $10^{11}$ particles/body. The patient may be any mammal, although it is contemplated that primate patients, and especially human patients, will benefit most from the methods of treatment. Other patients may include murine, canine, feline, bovine and equine species.

We contemplate that any AAV vector can be employed in the methods of this invention. Leading and preferred examples of such vectors for use in this invention are the AAV-2 basal vectors disclosed in Srivastava, PCT Patent Publication WO 93/09239. Most preferred are the vectors of the invention as disclosed herein. Such vectors comprise the two AAV ITRs (inverted terminal repeats) in which the authentic (i.e., native) D-sequences of the ITRs are modified by the substitution of nucleotides such that at least 5 authentic nucleotides and up to 18 authentic nucleotides, preferably at least 10 authentic nucleotides up to 18 authentic nucleotides, most preferably 10 authentic (i.e., native) nucleotides, are retained and the remaining nucleotides of the D-sequence are deleted or replaced with non-native, i.e., exogenous nucleotides. One preferred sequence of 5 native nucleotides that are retained is 5' CTCCA 3'. The authentic (i.e., native) D-sequences of the AAV ITRs are sequences of 20 consecutive nucleotides in each AAV ITR (i.e., there is one sequence at each end) which are not involved in HP formation. The exogenous or non-native replacement nucleotide may be any nucleotide other than the nucleotide found in the native D-sequence in the same position. For example, appropriate replacement nucleotides for native D-sequence nucleotide C are A, T and G and appropriate replacement nucleotides for native D-sequence nucleotide A are T, G and C. The construction of four such vectors is exemplified in Example 4, to wit, preferred vectors pD-5, pD-15 and pD-20, and most preferred vector pD-10, using the vector pXS-22 as starting material.

Other employable exemplary vectors are pWP-19, pWN-1 both of which are disclosed in Nahreini, *Gene* 124

(1993) 257–262. Another example of such an AAV vector is psub201. See Samulski, *J. Virol.* 61 (1987) 3096. Another example is the Double-D ITR vector. How to make the Double-D ITR vector is disclosed in U.S. Pat. No. 5,478, 745. Still other vectors are those disclosed in Carter, U.S. Pat. No. 4,797,368; and Muzyczka, U.S. Pat. No. 5,139,941, Chartejee, U.S. Pat. No. 5,474,935, and Kotin, PCT Patent Publication WO 94/28157. Yet a further example of an AAV vector employable in the methods of this invention is SSV9AFABTKneo, which contains the AFP enhancer and albumin promoter and directs expression predominantly in the liver. Its structure and how to make it are disclosed in Su, Selective killing of AFP-positive hepatocellular carcinoma cells by adeno-associated virus transfer of the herpes simplex virus thymidine kinase gene, *Human Gene Therapy* 7 (1996) 463–470. The disclosures of these scientific articles, U.S. Patents and patent publications are herein incorporated by reference.

Although not an absolute requirement for the practice of the invention, in a further embodiment, the AAV vectors of the invention may contain a liver specific promoter to maximize the potential for liver specific expression of the exogenous DNA sequence contained in the vectors. The promoter is operably linked to the nucleic acid encoding the therapeutic molecule upstream from the latter and between the AAV vector sequences (for example between the inverted terminal repeats in psub201or downstream of the Double D ITR sequence) Preferred liver specific promoters include the hepatitis B X-gene promoter and the hepatitis B core protein promoter. These liver specific promoters are preferably employed with their respective enhancers. The enhancer element can be linked at either the 5' or the 3' end of the nucleic acid encoding the therapeutic molecule. The hepatitis B X gene promoter and its enhancer can be obtained from the viral genome as a 332 base pair EcoRV-NcoI DNA fragment employing the methods described in Twu, *J. Virol.* 61 (1987) 3448–3453. The hepatitis B core protein promoter can be obtained from the viral genome as a 584 base pair BamHI-BglII DNA fragment employing the methods described in Gerlach, *Virol* 189 (1992) 59–66. It may be necessary to remove the negative regulatory sequence in the BamHI-BglII fragment prior to inserting it. Other liver specific promoters include the AFP (alpha fetal protein) gene promoter and the albumin gene promoter, as disclosed in EP Patent Publication 0 415 731, the α-1antitrypsin gene promoter, as disclosed in Rettenger, *Proc. Natl. Acad. Sci.* 91 (1994) 1460–1464, the fibrinogen gene promoter, the APO-A1 (Apolipoprotein A1) gene promoter, and the promoter genes for liver transference enzymes such as, for example, SGOT, SGPT and γ-glutamyl transferase. See also PCT Patent Publications WO 90/07936 and WO 91/02805.

We also contemplate that any hepatic disease or any defect in hepatic function, whether inherited or acquired, is susceptible to treatment with the methods of the invention. Exemplary hepatic diseases or defects in hepatic function include hepatocellular carcinoma, jaundice, infectious hepatitis, alcohol liver damage, including alcohol induced cirrhosis, and non-alcohol induced liver cirrhosis.

We also contemplate that any inherited or acquired disease or defect, the treatment of which requires administration of a therapeutic molecule that is normally made in the liver, is susceptible to treatment with the methods of the invention. Exemplary inherited diseases include familial hypercholesterolemia, which is caused by an LDL receptor deficiency, phenylketonuria, which is caused by a phenylalanine hydroxylase deficiency, urea cycle disorders, organic acid disorders, Wilson's disease, tyrosinemia, $\alpha_1$-antitrypsin deficiency and hyperammonemia which is caused by an inherited deficiency of ornithine transcarbamylase function. Exemplary acquired diseases include non-familial hypercholesterolemia and other hyperlipoproteinemias.

We also contemplate that the methods described here find use in treating any disease or condition in which the therapeutic substance, for example a secretory protein, is advantageously expressed in the liver in order to, for example, obtain systemic administration via entry into the circulatory system through the hepatic system. Genes encoding any of the cytokines and immunomodulatory proteins described here can be expressed in an AAV vector to achieve liver specific in vivo expression. Forms of these cytokines other than the forms mentioned here that are known to the skilled artisan can be used. For instance, nucleic acid sequences encoding native IL-2 (interleukin 2) and γ-interferon can be obtained as described in U.S. Pat. Nos. 4,738,927 and 5,326,859 respectively, while useful mutants of these proteins can be obtained as described in U.S. Pat. No. 4,853, 332. As an additional example, nucleic acid sequences encoding the short and long forms of M-CSF (macrophage colony stimulating factor) can be obtained as described in U.S. Pat. Nos. 4,847,201 and 4,879,227 respectively. AAV vectors expressing cytokine or immunomodulatory genes can be produced as described here.

AAV vectors producing a variety of known polypeptide hormones and growth factors can be used in the methods of the invention to produce therapeutic expression of these proteins. Some such hormones, growth factors and other proteins are described in EP patent 0 437 478 B1 for instance. Nucleic acid sequences encoding a variety of hormones can be employed, including for example, human growth hormone, insulin, calcitonin, prolactin, follicle stimulating hormone, luteinizing hormone, human chorionic gonadotropin, thyroid stimulating hormone. AAV vectors expressing polypeptide hormones and growth factors can be prepared by methods known to those of skill in the art. As an additional example, nucleic acid sequences encoding different forms of human insulin can be isolated as described in EP patent publication 026598 or 070632 and incorporated into AAV vectors as described here.

Any of the polypeptide growth factors can also be administered therapeutically by liver specific expression in vivo with an AAV vector. For instance, different forms of IGF- 1 and IGF-2 growth factor polypeptides are well known in the art and can be incorporated into AAV vectors for liver specific expression. See EP patent 0 123 228 B1. Liver specific expression of different forms of fibroblast growth factor can also be effected by the methods of the invention. See U.S. Pat. Nos 5,464,774; 5,155,214 and 4,994,559.

There are a number of proteins useful for treating hereditary disorders that can be expressed by the methods of the invention. Many genetic diseases caused by inheritance of defective genes result in the failure to produce normal gene products, for example, severe combined immunodeficiency (SCID), hemophilia A, hemophilia B, adenine deaminase deficiency, Gaucher's syndrome, hereditary lactose intolerance and inherited emphysema. Also contemplated are diseases that are caused by the inability of the gene to produce adequate levels of the appropriate hormone, such as diabetes and hypopituitarism.

Liver specific expression of Factor VIII or Factor IX, useful for the treatment of blood clotting disorders such a hemophilia, is obtainable using the methods of the invention. PCT Patent Publication WO 96/21014 describes Factor VIII and HGH (human growth hormone) constructs for retroviral expression which could readily adapted by the skilled artisan for AAV expression. The Factor VIII minigene (see EP Patent Publication 232 112 and PCT Patent Publication WO 91/07490) could advantageously be employed for AAV expression. Also contemplated is the expression of lactase for the treatment of hereditary lactose intolerance, ADA for the treatment of ADA deficiency and α-1 antitrypsin for the treatment of α-1 antitrypsin deficiency. See Ledley, *J. Pediatrics* 110: (1987) 157–174; Verma, *Scientific American* (Nov. 1987) pp. 68–84 and PCT Patent Publication WO095/27512.

There are a variety of other proteins of therapeutic interest that can be expressed in a liver specific manner using the methods of the invention. For instance sustained expression of tissue factor inhibitory protein (TFPI) is useful for the treatment of conditions including sepsis and DIC and in preventing reperfusion injury. See PCT Patent Publications WO 93/24143, WO 93/25230 and WO 96/06637. Nucleic acid sequences encoding various forms of TFPI can be obtained, for example, as described in U.S. Pat. Nos. 4,966,852; 5,106,833 and 5,466,783, and can be incorporated into AAV vectors as described here.

Other proteins of therapeutic interest such as erythropoietin (EPO) and leptin can be expressed in the liver by AAV vectors according to the methods of the invention. EPO is useful in gene therapy treatment of a variety of disorders including anemia. See PCT Patent Publication WO 95/13376. Gene therapy delivery of the leptin gene and its use in the treatment of obesity is described in PCT Patent Publication WO 96/05309. AAV vectors expressing EPO or leptin can readily be produced and liver specific expression attained employing the described methods. Other exemplary proteins and polypeptides include the cytokines such as interleukin (IL)-1, IL-2, IL-3, IL-4, IL-5, IL-6, IL-7, IL-8, IL-9, IL-10, IL-11, IL-12, IL-13, IL-14 and IL-15, α-interferon, β-interferon, the γ-interferons, GM-CSF, the tumor necrosis factors (TNFs), CD3, ICAM-1, LFA-1, LFA-3, the chemokines including RANTES 1α, MIP-1α, MIP-1β (see Cocchi, Science 720 (1996) 1811–1815) or analogs of such proteins. Because soluble forms of receptors can often behave as antagonists, as can mutated forms of the factors themselves, the nucleic acid sequences of therapeutic interest may also be agonists, antagonists or ligands for these proteins and polypeptides.

Even more proteins and polypeptides of therapeutic interest that can be expressed in liver specific fashion employing the AAV vectors and methods of the invention include Protein S and Gas6, thrombin, Coagulation Factor Xa, CSF-1 or M-CSF, IGF-1, IGF-2, acidic FGF, basic FGF, keratinocyte growth factor (KGF), TGF, platelet derived growth factor (PDGF), epidermal growth factor (EGF), hepatocyte growth factor (HGF) and HGF activators, PSA, nerve cell growth factor (NCGF), glial cell derived nerve growth factor (GDNF), VEGF, Arg-vasopressin, thyroid hormones, azoxymethane, triiodothyronine, LIF, amphiregulin, soluble thrombomodulin, stem cell factor, osteogenic protein 1, the bone morphogenic proteins, MGF, MGSA, heregulins and melanotropin. Growth factors can also be used in combination with mixtures consisting of one or several of, for example, DGF, IGF, PDGF, FGF or KGF. The full length growth factor can be employed or forms of the growth factor, such as active fragments, truncated forms and analogues can be employed. By "active fragment" we mean a polypeptide containing less than a full-length sequence that retains sufficient biological activity to be used in the methods of the invention. By "analogue" we mean truncated forms, splice variants, variants with amino acid substitutions, deletions or additions, alleles and derivatives of the mature protein or polypeptide which possess one or more of the native bioactivities of the full length protein or polypeptide. Thus, polypeptides that are identical or contain at least 60%, preferably, 70%, more preferably 80% and most preferably 90% amino acid sequence homology to the amino acid sequence of the mature protein wherever derived, from human or non-human sources are included within this definition. For example, a preferred truncated form of KGF is described in PCT Patent Publication WO 95/10434. See also PCT Patent Publication WO 90/08771 and U.S. Pat. No. 5,096,825 relating to human EGF.

The growth factor polypeptides, fragments and analogues can be produced by isolation from naturally occurring sources, polypeptide chain synthesis by peptide synthesis methods and production or recombinant proteins. These methods are well known to those of skill in the art. For example, production of recombinant PDGF is described in U.S. Pat. Nos. 5,045,633 and 4,769,328 and production of recombinant FGF and analogues is described in U.S. Pat. Nos., 5,229,501; 5,331,095 and 5,143,829.

A variety of other disorders can be treated by the methods of the invention. For example, production of apolipoprotein E or apolipoprotein A, useful in treating hyperlipidemia, can be attained via administration of the liver specific AAV vectors of the invention. See Breslow, *Biotechnology* 12 (1994) 365. Sustained production of angiotensin receptor inhibitor (see Goodfriend, *N. Engl. J. Med.* 334 (1996) 1469) or of angiostatin useful in the treatment of tumors (see O'Reilly, *Nature Med.* 2 (1996) 689) can be attained.

Nucleic acid sequences that encode the above-described proteins and polypeptides are obtainable from a variety of sources. For example, plasmids containing sequences the encode altered cellular products may be obtained form a depository such as the American Type Culture Collection (ATCC, Rockville, Md.) or from commercial sources such as Advanced Biotechnologies (Columbia, Md.) and British Bio-Technology Limited (Cowley, Oxford, Great Britain). Exemplary plasmids include ATCC Nos. 41000 and 41049 containing muteins of ras. Other nucleic acid sequences that encode the above-described proteins and polypeptides, as well as other nucleic acid molecules such as antisense sequences and ribozymes that are advantageously used in the invention may be readily obtained from such public sources. Exemplary are BBG12 containing the full length GM-CSF coding sequence, BBG6 containing the γ-interferon coding sequence, ATCC No. 39656 containing sequences encoding TNF, ATCC No. 20663 containing sequences encoding α-interferon, ATCC Nos. 31902 and 39517 containing sequences encoding P-interferon, ATCC No. 67024 containing the interleukin-1b coding sequence, ATCC Nos. 39405, 39452, 39516, 39626 and 39673 containing sequences encoding interleukin-2, ATCC No. 57592 containing sequences encoding interleukin-4, ATCC Nos. 59394 and 59395 containing sequences encoding interleukin-5 and ATCC 67153 containing sequences encoding interleukin-6. Molecularly cloned genomes encoding the hepatitis B virus are obtainable from the ATCC. ATCC No. 45020 contains the total genomic DNA of hepatitis B # (with correctable errors), extracted from purified Dane particles, in the BamHI site of pBR322. See Blum TIG 5 (1989) 154–158 and Moriarty, *Proc. Natl. Acad. Sci.* 78 (1981) 2606–2610. Alternatively, cDNA sequences for use with the invention are obtainable from cells that express or contain the sequences. Briefly, within one embodiment, MRNA from a cell that expresses the gene of interest is reverse transcribed with reverse transcriptase using oligo dT or random primers. The single stranded cDNA may then be amplified by PCR (see U.S. Pat. Nos. 4,683,202; 4,683,195 and 4,800,159, *PCR Technology: Principles and Applications for DNA Amplification*, Erlich (ed.), Stockton Press, 1989) using oligonucleotide primers complementary to sequences on either side of desired sequences. In particular, a double stranded DNA is denatured by heating in the presence of heat stable Taq polymerase, sequence specific DNA primers, ATP, CTP, GTP and TTP. Soluble-stranded DNA is produced when synthesis is complete. This cycle may be repeated many times resulting in a factorial amplification of the desired DNA. Nucleic acid sequences may also be synthesized de novo, for example on an Applied Biosystems Inc. DNA synthesizer.

In another embodiment, AAV hybrid (i.e., chimeric) vectors are provided containing the DNA sequence, or functional fragment thereof, encoding hepatitis B surface antigen and the DNA sequence encoding the AAV capsid protein. An oligonucleotide sequence that corresponds to this HBV surface antigen peptide is blunt-ended and ligated at the 5' end of the AAV VP-1 gene. Specifically, the 27 amino acid sequence of HBV surface antigen corresponding to amino acids 20–47 of the preS1 region (see, Ishikawa, *Proc. Natl. Acad. Sci.* 92 (1995) 6259–6263; Klingmuller, *J. Virol.* 67 (1993) 7414–7422 and Neurath, *Cell* 46 (1986) 429–436 and *Virol.* 176 (1990) 448–457) are fused in-frame to the AAV viral capsid VP-1 gene (see Srivastava, *J. Virol.* 45 (1983) 555–564). Nucleic acids encoding therapeutic molecules cloned within recombinant AAV vectors may be packaged into recombinant AAV virions using this AAV-HBV chimeric helper vector. The AAV-2 capsid gene has been cloned and is available. See Samulski, *J. Virol.* 63 (1989) 3822–3828. But capsid genes from any AAV, specifically from AAV-1, AAV-3 or AAV-4, can be employed. For a general review of the molecular biology, structure and gene products of HBV see Yoffe, Progress and perspectives in human hepatitis B virus research. *Prog. Med. Virol.* 40 pp.107–140 (Melnick, J. L. ed.) 1993.

To establish integration of the vector into the chromosome of a host cell, host cells are transfected with the vector or infected with mature virions containing the vector. Methods of transfection are well-known in the art and include, for example, naked DNA transfection, microinjection and cell fusion. Virions can be produced by coinfection with helper virus such as adenovirus, herpes virus or vaccinia virus. Following coinfection with the vector and a helper virus, the host cells are isolated and the helper virus is inactivated. The resulting helper free stocks of virions are used to infect host cells. Alternatively, virions are produced by cotransfecting helper virus-infected cells with the vector and a helper plasmid. The plasmid will contain the parvovirus rep gene and non-AAV ITRs, for example adenovirus ITRs. Following cotransfection, mature virions are isolated using standard methods and any contaminating adenovirus inactivated using methods known to skilled artisans. The resulting mature virions can be used to infect host cells in the absence of helper virus.

Methods of making recombinant AAV vectors and packaging cell lines, purification methods, rescue methods and methods of generating high-titer vector stocks are known in the art. See for example, Samulski, A recombinant plasmid from which an infectious adeno-associated virus genome can be excised in vitro and its use to study viral replication, *J. Virol.* 61 (1987) 3096–3101 and helper-free stocks of recombinant adeno-associated viruses: Normal integration does not require viral gene expression, *J. Virol.* 63 (1989) 3822–3828; McLaughlin, Adeno-associated virus general transduction vectors: Analysis of proviral structures, *J. Virol.* 62 (1988) 1963–1973; Flotte, An improved system for packaging recombinant adeno-associated virus vectors capable of in vivo transduction, *Gene Therapy* 2 (1995) 29–37; Holscher, Cell lines inducibly expressing the adeno-associated virus (AAV) rep gene: Requirements for productive replication of rep-negative AAV mutants, *J. Virol.* 68 (1994) 7169–7177 and High-level expression of adeno-associated virus (AAV) Rep78 protein is sufficient for infectious-particle formation by a rep-negative AAV mutant, *J. Virol.* 69 (1995) 6880–6885; Yang, Characterization of cell lines that inducibly express the adeno-associated virus Rep proteins, *J. Virol.* 68 (1994) 4847–4856; Ponnazhagan, Alternative strategies for generating recombinant AAV vectors, *VIth Parvovirus Workshop*, Montpellier, France, p. 71(1995); Luhovy, Stable transduction of recombinant adeno-associated virus into hematopoietic stem cells from normal and sickle cell patients, *Bio. Blood Marrow Transpl.* 2 (1996) 24–30; Tamayose, A new strategy for large-scale preparation of high-titer recombinant adeno-associated virus vectors by using sulfonated cellulose column chromatography, *Hum. Gene Therap.* 7 (1996) 507–513; Maxwell, Improved method for production of recombinant AAV and determination of infectious titer, *VIth Parvovirus Workshop*, Montpellier, France, p72 (1995); Chiorini, High-efficiency transfer of the T cell co-stimulatory molecule B7–2 to lymphoid cells using high-titer recombinant adeno-associated virus vectors, *Hum. Gene Therap.* 6 (1995) 1531–1541;and Colosi, AAV vectors can be efficiently produced without helper virus, *Blood* 10 (1995) 627a.

The vector or virions can be incorporated into pharmaceutical compositions for administration to mammalian patients, particularly humans. The vector or virions can be formulated in nontoxic, inert, pharmaceutically acceptable aqueous carriers, preferably at a pH ranging from 3 to 8, more preferably ranging from 6 to 8. Such sterile compositions will comprise the vector or virion containing the nucleic acid encoding the therapeutic molecule dissolved in an aqueous buffer having an acceptable pH upon reconstitution. Such formulations comprise a therapeutically effective amount of a AAV vector or virion in admixture with a pharmaceutically acceptable carrier and/or excipient, for example saline, phosphate buffered saline, phosphate and amino acids, polymers, polyols, sugar, buffers, preservatives and other proteins. Exemplary amino acids, polymers and sugars and the like are octylphenoxy polyethoxy ethanol compounds, polyethylene glycol monostearate compounds, polyoxyethylene sorbitan fatty acid esters, sucrose, fructose, dextrose, maltose, glucose, mannitol, dextran, sorbitol, inositol, galactitol, xylitol, lactose, trehalose, bovine or human serum albumin, citrate, acetate, Ringer's and Hank's solutions, cysteine, arginine, carnitine, alanine, glycine, lysine, valine, leucine, polyvinylpyrrolidone, polyethylene and glycol. Preferably, this formulation is stable for at least six months at 4° C.

The virions can be systemically administered by intravenous injection. The dosage regimen will be determined by the attending physician or veterinarian considering various factors known to modify the action of drugs such as, for example, the physical condition of the patient, the severity of the condition, body weight, sex, diet, time of administration and other clinical factors. Generally, the regimen should be in the range of about $10^9$ to about $10^{11}$ particles per body. A preferred dose is about $10^{10}$ particles per body. The number of doses administered may vary, depending on the above mentioned factors.

The AAV vector or virions can also be administered ex vivo employing art recognized methods, for example, by electroporation following the procedures of Chakrabarti, *J. Biol. Chem.* 264 (1989) 15494–15500 or by protoplast delivery following the procedures of Kaneda, *Science* 243 (1989) 375–78 and Ferguson, *J. Biol. Chem* 261 (1986) 14760–14763. Alternatively, hepatocyte precursor cells can be transduced with a vector of the invention, grown in tissue culture vessels, removed and introduced into the patient surgically by grafting or transplantation. The precursor cells can be attached to supports such as microcarrier beads that are injected into the peritoneal space of the patient or directly into the liver, into the portal venous system or into the spleen. The patient's liver cells may be obtained through liver biopsy, partial hepatectomy or from specimens harvested for orthotopic liver transplantation, purified and grown in culture. AAV vectors may be introduced into the liver cells by exposure to the virus and the liver cells reintroduced into the patient by grafting or by placing the cells in the abdominal cavity in contact with the unremoved portion of the patient's liver. Such methods are known in the art. See, for example, Chang, Gene Therapy: Applications to the Treatment of Gastrointestinal and Liver Diseases, *Gastroenterology* 106 (1994) 1076–1084. For ex vivo administration, the dosage regimen should be in the range of 1 to 100 m.o.i., preferably in the range of 5 to 20 m.o.i. The dosage regimen will be determined by the attending physician considering various factors known to modify the action of drugs such as for example, physical condition, body weight, sex, diet, severity of the condition, time of administration and other clinical factors. The number of doses administered may vary, depending on the above mentioned factors.

The liver specific delivery methods of the invention may be employed with or without pretreatment of the liver. Pretreatment includes benign hyperplasia, which can be induced by treatment with HGF and/or transforming growth factorα. See Lui, *Hepatology* 19 (1994) 1521. Different forms of HGF useful in inducing liver cell proliferation are known in the art and can be employed. See for example EP patent publication EP 0 461 560. HGF can also be produced and administered to induce liver cell proliferation in vivo as described in Joplin, *J. Clin. Invest.* 90 (1992) 1284. Liver cells can also be stimulated by administration of agents that mediate or potentiate the activation of endogenous HGF. HGF is produced as a single chain protein that is inactive as a growth factor. Single chain HGF is subsequently cleaved into a two-chain form that is biologically active. Enzymes that are shown to convert single-chain HGF to its bioactive form are useful for inducing liver cell proliferation. Therefore, these enzymes can be administered either alone or in combination with exogenous HGF to enhance liver proliferation. Exemplary enzymes include coaglation factor XIIa, HGF activator, HGF converting enzyme, urokinase and tissue plasminogen activator. For example, HGF and urokinase can be co-formulated and administered by intravenous injection or mixed immediatedly prior to injection. If co-formulated, storage at low pH would advantageously minimize the activity of urokinase. See PCT Patent Publication WO 96/21014 entitled Production and Administration of High Titer Recombinant Retroviruses.

In another embodiment of the invention the AAV vector is co-administered with a cholesterol lowering drug to a primate patient suffering from hypercholesterolemia. A preferred cholesterol lowering drug is M-CSF. See U.S. Pat. Nos. 5,021,239 and 5,019,381. Other preferred cholesterol lowering drugs include niacin, gemfibrozil, lovastatin and mevacor.

DETAILED DESCRIPTION

Figure 1:
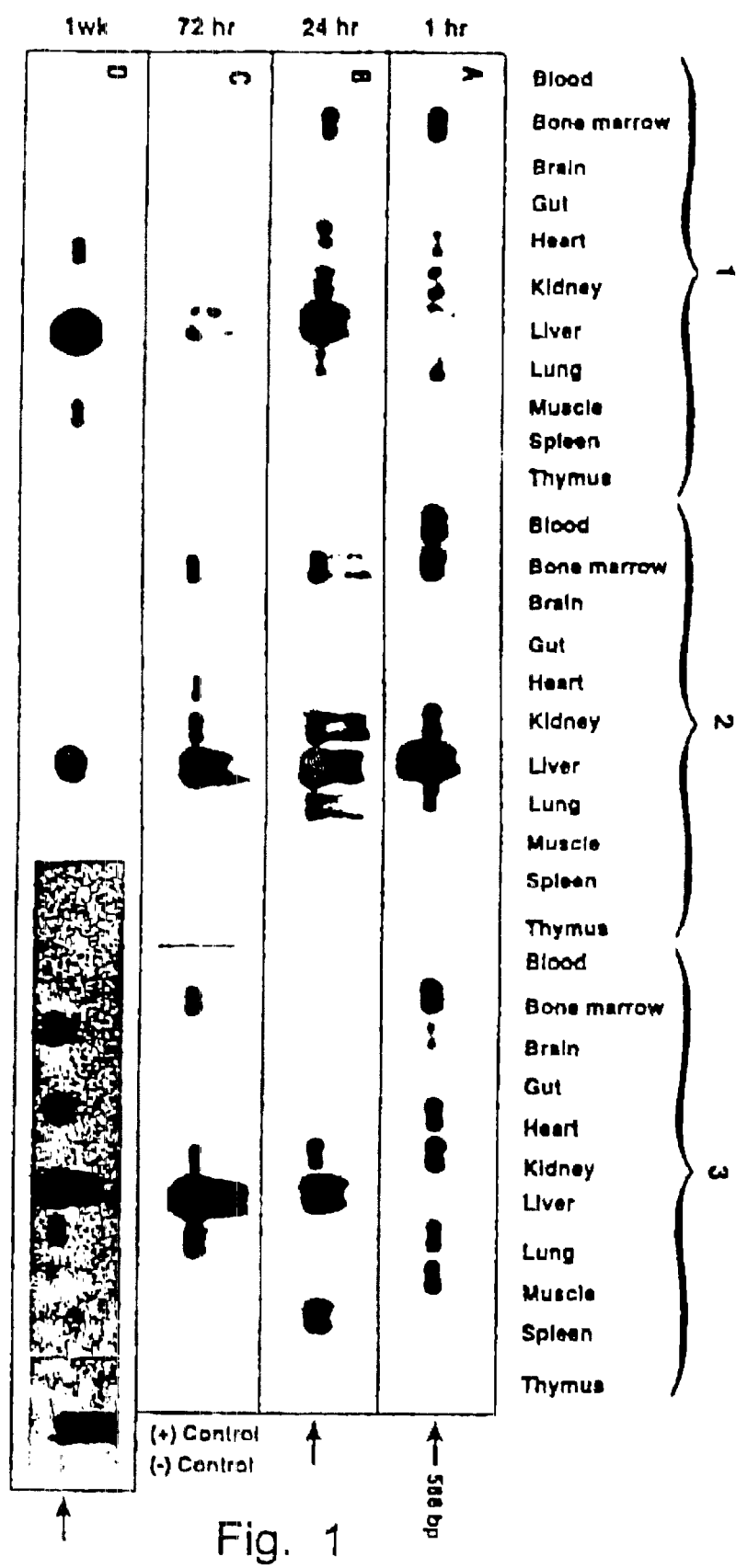
FIG. 1: Illustration of the Southern blot analysis of the PCR-amplified DNA fragments of the vCMVp-lacZ vector administered to mice as described in Example 1, in various murine tissues.

In murine mammalian patients, the fate of AAV vectors was followed after direct intravenous injection and it was surprisingly found that the AAV vectors possess organtropism for liver. Our AAV vectors contained the lacZ reporter gene or the human globin gene. In mice administered the lacZ reporter gene containing AAV vectors, expression occured in hepatocytes but a cytotoxic T lymphocyte response against βGal was not detected. The recombinant AAV vectors, when directly injected intravenously in mice, accumulated predominantly in liver cells.

The AAV recombinant virus stocks containing the CMV promoter ($CMV_p$) driven lacZ gene (vCMVp-lacZ) cloned in between AAV inverted terminal repeats (ITR) and the AAV recombinant virus stocks containing the genomic copy of the normal human $^A$γ-globin gene driven by the human β-globin promoter (βp) plus an upstream Hypersensitive site 2 enhancer element cloned in between AAV ITR were generated from their respective recombinant plasmids by the methods described in Samulski, Helper-free Stocks of Recombinant Adeno-associated Viruses: Normal Integration Does Not Require Viral Gene Expression, *J. Virol.* 63 (1989) 3822–3828; Nahreini,Versatile Adeno-associated Virus 2-based Vectors for Constructing Recombinant Virions, *Gene* 124 (1993) 257–262; Zhou, Adeno-associated Virus 2-mediated High Efficiency Gene Transfer into Immature and Mature Subsets of Hematopoietic Progenitor Cells in Human Umbilical Cord Blood, *J. Exp. Med.* 179 (1994) 1867–1875; Ponnazhagan, Lack of Site-specific Integration of the Recombinant Adeno-associated Virus Genomes in Human Cells, 5th *Parvovirus Workshop*, Crystal River, Fla., USA p.P1–29 (1993); Ponnazhagan, Adeno-associated Virus 2-mediated Transduction of Murine Hematopoietic Cells and Long-term Expression of a Human Globin Gene in Vivo, 6th *Parvovirus Workshop*, Montpellier, France. p29 (1995); and Ponnazhagan, Differential Expression in Human Cells from the P6 Promoter of Human Parvovirus B 19 Following Plasmid Transfection and Recombinant Adeno-associated Virus 2 (AAV2) Infection: Human Megakaryocytic Leukaemia Cells Are Non-Permissive for AAV Infection, *J. Gen. Virol.* 77 (1996) 1111–1122. The viral stocks were purified on CsCl density gradients following the protocol described in Wang, Parvovirus B19 Promoter at Map Unit 6 Confers Replication Competence and Erythroid Specificity to Adeno-associated Virus 2 in Primary Human Hematopoietic Progenitor Cells, *Proc. Natl. Acad. Sci.* 92 (1995) 12416–12420. Titers were determined on quantitative DNA slot blots as described in Srivastava, Parvovirus B19-induced. Perturbation of Human Megakaryocytopoiesis In Vitro, *Blood* 76 (1990) 1997–2004; Srivastava, Construction of a Recombinant Human Parvovirus B19: Adeno-associated Virus 2 (AAV) DNA Inverted Terminal Repeats Are Functional in an AAV-B19 Hybrid Virus, *Proc. Natl. Acad. Sci.* 86 (1989) 8078–8082.; Nahreini and Srivastava, Rescue of the Adeno-associated Virus 2 Genome Correlates with Alterations in DNA-modifying Enzymes in Human Cells, *Intervirol.* 33 (1992) 109–115.; Zhou, Adeno-associated Virus 2-mediated Gene Transfer in Murine Hematopoietic Progenitor Cells, *Exp. Hematol.* 21 (1993) 928–933; Zhou, Adeno-associated Virus 2-mediated High Efficiency Gene Transfer into Immature and Mature Subsets of Hematopoietic Progenitor Cells in Human Umbilical Cord Blood, *J. Exp. Med.* 179 (1994) 1867–1875 and Zhou, Adeno-associated Virus 2-mediated Transduction and Erythroid Cell Specific Expression of a Human β-globin Gene, *Gene Therapy* 3 (1996) 223–229.

These highly purified recombinant AAV vectors were administered to C57B1/6 mice by direct intravenous injection into the tail vein.

EXAMPLE 1

Highly purified recombinant AAV vectors containing the cytomegalovirus (CMV) promoter-driven lacZ gene (vCMVp-lacZ) were directely injected into C57B1/6 mice. Approximately 1 ×10$^{10}$ viral particles of vCMVp-lacZ were injected intravenously into the tail-vein of 12 animals in four groups of three animals each. These animals were sacrificed at various times post-injection (p.i.), and equivalent amounts of tissues from various organs were examined for the presence of the recombinant AAV viral genome by polymerase-chain-reaction (PCR) amplification using a lacZ-specific primer-pair followed by Southern blot analysis.

Approximately 1 ×10$^{10}$ particles of the vCMVp-lacZ r-virus were injected in 0.2 ml Iscove's-modified Dulbecco's medium into the tail-vein of 8-week old C57B1/6 mice. Three animals per group were sacrificed at 1 hour, 24 hours, 72 hours, and 1 week p.i. Individual tissues and organs were obtained, rinsed extensively with phosphate-buffered-saline, and equivalent amounts were used in a 35-cycle PCR-amplification reaction using the lacZ-specific primer-pair (5'-GATGAGCGTGGTGGTTATG (SEQ ID NO:1), 5'-TACAGCGCGTCGTGATTAG)(SEQ ID NO:2). Plasmids pCMVp-lacZ (Ponnazhagan et al., 1996) and pUC19 (Sambrook, Fritsch, and Maniatis, *Molecular Cloning: A Laboratory Manual*, CSHL Press, Cold Spring Harbor, N.Y., 1989) were used as positive and negative controls, respectively. The PCR products were electrophoresed on 1% agarose gels and analyzed on Southern blots (Southern, Detection of specific sequences among DNA fragments separated by gel electrophoresis. *J. Mol. Biol.* 98 (1975) 503–517) using a lacz-specific $^{32}$P-labeled DNA probe.

The results of the Southern blot analysis are shown in FIG. 1. The recombinant AAV genomes were detected predominantly in the liver tissues up to 1-week p.i. in each group of animals. The arrows indicate the 588-bp lacz-specific DNA fragment.

EXAMPLE 2

The results in Example 1 were corroborated by injecting recombinant vHS2-βp-$^A$γ-globin virions under conditions identical to those in Example 1 and examining tissues from various organs seven weeks p.i. using the same techniques, but employing a β-globin promoter-$^A$γ-globin gene-specific primer-pair.

Highly purified recombinant AAV vectors containing the human β-globin promoter-driven human $^A$γ-globin gene containing the DNase hypersensitive-site 2 (HS-2) enhancer element (see Tuan, An erythroid specific, development stage-independent enhancer far upstream of the human "β-like globin" genes, *Proc. Natl. Acad. Sci.* 86 (1989) 2554–2559) from the locus control region (LCR) from the human β-globin gene cluster (vHS2-βp-$^A$γ-globin) were directly injected into C57B1/6 mice.

Figure 2:
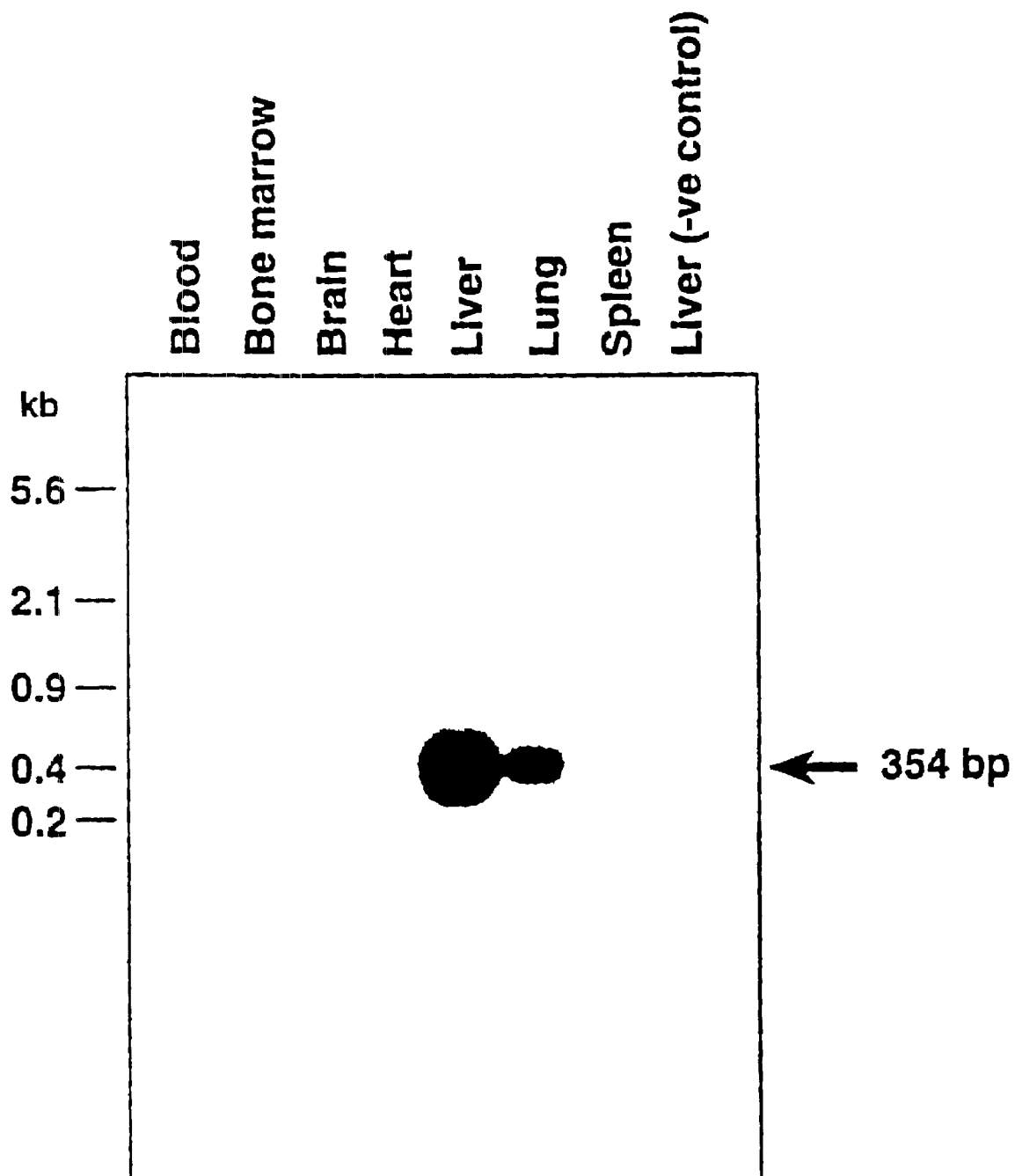
FIG. 2: Illustration of the Southern blot analysis of the PCR-amplified DNA fragments of the vHS2-βp-$^A$γ-globin vector administered to mice as described in Example 2, in various murine tissues.

Approximately 1 ×10$^{10}$ particles of the vHS2-βp-$^A$γ-virus were injected i.v. as described in Example 1. Seven weeks p.i., the various organs were obtained and analyzed for the presence of the r-viral genome using the human β-globin promoter (5'-GATGGTATGGGGCCAAGAGA (SEQ ID NO: 3))- and $^A$γ-globin gene (5'-GGGTTTCTCCTCCAGCATCT (SEQ ID NO: 4))-specific oligodeoxynucleotide primer pair. Liver tissues obtained from a mock-injected mouse was also included as a negative control. The Southern blot results are shown in FIG. 2. The arrow indicates the 354-bp human γ-globin-specific DNA fragment.

Figure 3:
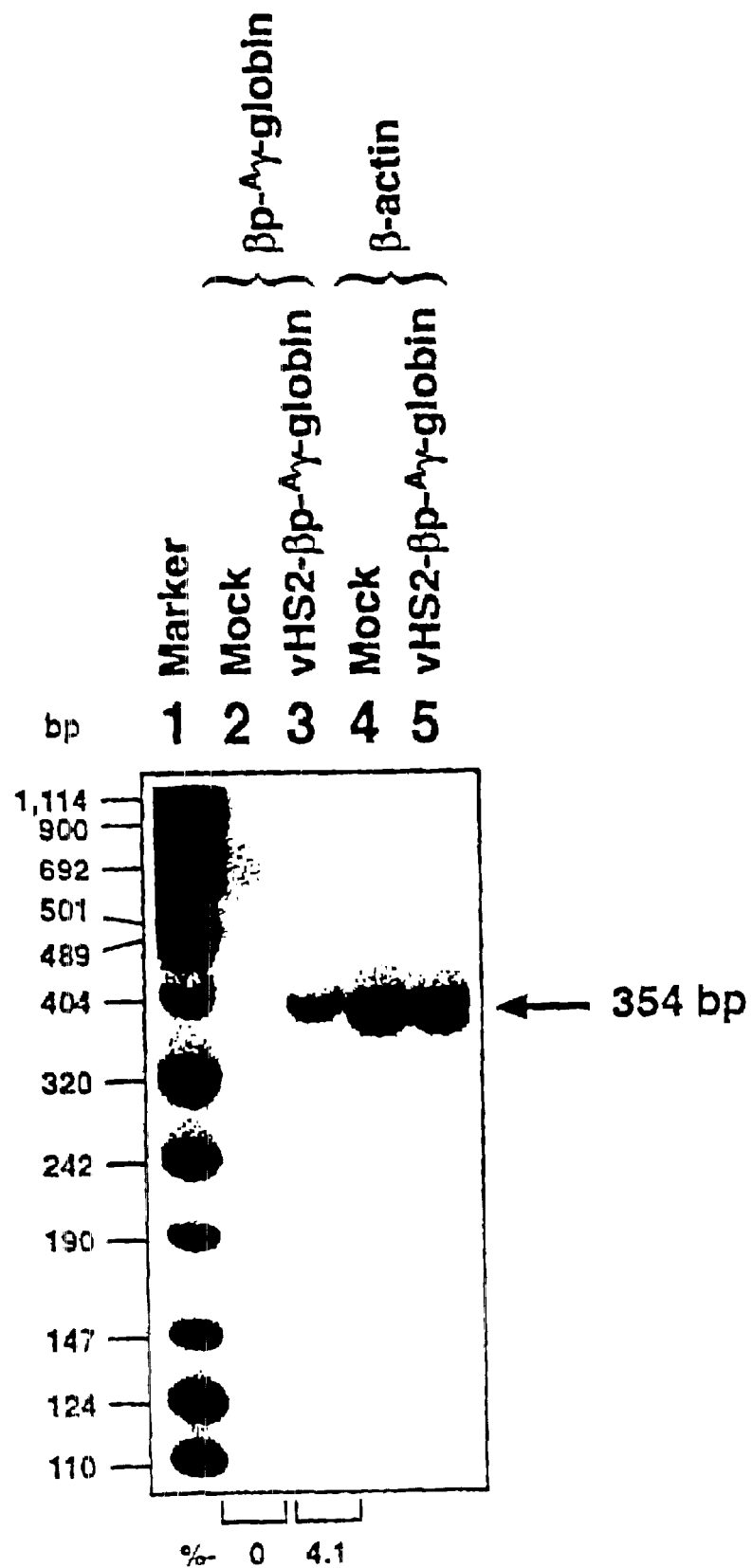
FIG. 3: Illustration of autoradiogram of semi-quantitative PCR amplification results, as detailed in Example 2.
Figure 4:
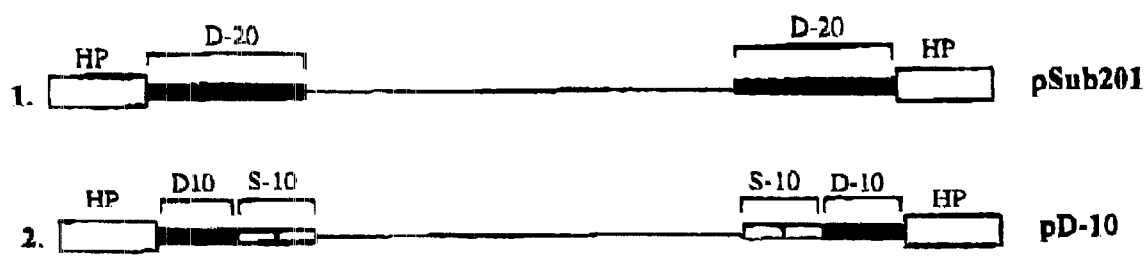
FIG. 4: Schematic structures of pSub201and pD-10 recombinant AAV vectors, as detailed in Example 5. The D-sequence is shown as a shaded box in plasmid pSub201. In plasmid pD-10, the distal 10 nucleotides in the D-sequence have been replaced by a substitute (s)-sequence.

We then investigated copy number of the vHS2-βp-$^A$γ-globin vector in liver cells. Equivalent amounts of DNA isolated from the liver of mock-injected and vHS2-βp-$^A$γ-globin virus-injected mice were used in a semi-quantitative PCR amplification assay using either the human β-globin promoter-$^A$γ-globin gene-specific oligodeoxynucleotide primers or the mouse β-actin-specific oligodeoxynucleotide primers. Approximately equivalent amounts of liver tissue from each animal were lysed in a buffer containing 10 mM Tris. HCl/50 mM KCl/2.5 mM MgCl2/0.5% Tween-20/100 μg proteinase K per ml at 55° C. overnight. The lysates were heated at 90° C. for 10 min to inactivate proteinase K, and 5 μl of each sample was subjected to a 30-cycle PCR amplification with the two sets of primer-pairs under identical conditions. The primers for amplifying the transduced human globin gene sequences were the same as those described in Example 1 and the primer sequences for the mouse β-actin gene were as follows: 5'-ACCTTCAACACCCCAGCCAT (SEQ ID NO: 5) and 5'-TCAGGCAGCTCATAGCTCTT (SEQ ID NO: 6). The primers were designed to yield a 354-bp DNA fragment from each sequence. The PCR reactions were performed in the presence of 2 μCi [α-$^{32}$P]dCTP (sp.act. 800 Ci/mmol) in each reaction mix. Ten percent of the DNA products from the human globin gene and a 15-fold diluted samples from the β-actin gene amplification reactions were analyzed on 6% polyacrylamide gels and autoradiographed. The relative intensities of the corresponding bands were determined by scanning the autoradiograms using the Photoshop 3.0 program. The transduced globin gene was detected in approximately 4% of liver cells seven weeks p.i. See FIG. 3.

EXAMPLE 3

We next examined whether the lacZ gene delivered by direct injection of the r-AAV was transcriptionally active. Livers from mock-injected and vCMVp-lacZ-injected C57B1/6 mice were obtained one week p.i., and cryopreserved. Tissue sections were fixed and stained with 5-bromo-4-chloro-3-indolyl-β-D-galactopyranoside (XGal) as described in Cheng, Separable Regulatory Elements Governing Myogenin Transcription in Mouse Embryogenesis, *Science* 261 (1993) 215–218 and visualized under a light microscope.

Livers were obtained one week p.i. and frozen immediately in iso-pentane at −40° C. Sections of 15 μm were prepared using a cryostat and fixed in a solution containing 2% formaldehyde/0.2% para-formaldehyde in phosphate-buffered saline (PBS, 135 mM NaCl/2.5 mM KCl/8 mM $Na_2HPO_4$/0.6 mM $KH_2PO_4$/0.55 mM dextrose/liter) for 5 min on ice, washed twice with PBS and stained overnight at 37° C. in a solution containing 5 mM $K_3Fe(CN)_6$/5 mM $K_4Fe(CN)_6$/1 mM $MgCl_2$/1 mg XGal in 1 ml of PBS, as described previously in Cheng, Separable regulatory elements governing myogenin transcription in mouse embryogenesis. *Science* 261 (1993) 215–218. Tissue sections were visualized under a light microscope (magnification ×40). No expression of the transgene occurred in liver cells from mock-injected animal. Expression of the lacZ gene was readily detected in liver hepatocytes.

EXAMPLE 4

Co-transfection of an rAAV vector containing the AAV ITRs and the nucleic acid sequence encoding a therapeutic molecule and a helper plasmid containing the necessary rep and cap functions into adenovirus-2 (Ad2) infected 293 cells was expected to eliminate homologous recombination events leading to the production of contaminating wild-type (wt) AAV during the production of recombinant vector stocks. However, contaminating "wild type-like AAV" particles have been observed in such stocks ranging from 0.1% to 10%.

To determine the mechanism of generation of contaminating wt AAV, stocks were amplified through four successive round of co-infection with Ad2 in 293 cells. Low molecular weight DNA fragments were isolated, digested with Bal I restriction endonuclease and molecularly cloned into a pBlueScript plasmid vector. AAV sequence-positive clones were subjected to nucleotide sequencing using T3 and T7 primers. Nucleotide sequence analysis of 12 independent clones revealed that most of the recombination events leading to the contaminating wt AAV involved 10 nucleotides in the AAV D-sequence distal to viral hairpin structures. In addition, by analyzing 22 different clones generated with a helper plasmid that lacks the Ad2 ITRs, we observed only a limited number of recombination sites and concluded that Ad2 ITRs play a role in illegitimate recombination with the AAV-ITRs that leads to generation of biologically active wild type-like AAV. Consequently, by removing the Ad2 ITRs from the helper plasmid, nearly 5-fold reduction in the illegitimate recombination frequency can be achieved.

The first 10 nucleotides in the D-sequence proximal to the AAV hairpin structures are essential for successful replication and encapsidation of the viral genome. See, Wang, *J. Virol.* 71: 3077–82 (1997). In each of the recombinant junctions sequenced, the same 10 nucleotides were retained. By deleting the distal 10 nucleotides in the D-sequence in the next generation of AAV vectors, the generation of the wt AAV-like particles in recombinant AAV vectors stocks can be reduced or eliminated. See Example 5 below for production of such vectors.

EXAMPLE 5

Four recombinant AAV vectors, pD-5, pD-10, pD-15 and pD-20, were constructed as follows. Plasmid pXS-22 can be employed as starting material. The plasmid pXS-22 can be obtained from a public depository or constructed following the methods described in Wang, *J. Mol. Biol.* 250 (1995) 573–580 using pSub210 as starting material. Plasmid pXS-22 contains only the right ITR (inverted terminal repeat): one hairpin and one D sequence. The D-sequence is that part of the AAV ITR which is not involved in HP formation. See Wang, supra. The D-sequence can be replaced by a substitute (S) sequence as described in Wang, *J. Virol.* 70 (1996) 1668–1677. The nucleotide sequences are as follows:

D-sequences:
  5' CTCCA TCACT AGGGG TTCCT (SEQ ID NO: 7)
  3' GAGGT AGTGA TCCCC AAGGA 5' (SEQ ID NO: 8)
S-sequence:
  5' CCAA TATTA GATCT GATAT CA 3' (SEQ ID NO: 9)
  3' GGTT ATAAT CTAGA CTATA GTGAT C 5' (SEQ ID NO: 10)

Four additional oligonucleotide sequences were synthesized which contained selected nucleotides identical to the authentic or native D-sequence in place of nucleotide in the S-sequence. These four oligonucleotides are:
D-5 oligonucleotide:
  5' CCAA CTCCA GATCT GATAT CACTT 3' (SEQ ID NO: 11) (bold=SEQ ID NO: 12)
  3' GGTT GAGGT CTAGA CTATA GTGAA GATC (SEQ ID NO: 13) (bold=SEQ ID NO: 14)
D-10 oligonucleotide:
  5' CCAA CTCCA TCACT GATAT CACTT 3' (SEQ ID NO: 15) (bold=SEQ ID NO: 16)
  3' GGTT GAGGT AGTGA CTATA GTGAA GATC 5' (SEQ ID NO: 17) (bold=SEQ ID NO: 18)
D-15 oligonucleotide:
  5' CCAA CTCCA TCACT AGGGG CACTT 3' (SEQ ID NO: 19) (bold=SEQ ID NO: 20)
  3' GGTT GAGGT AGTGA TCCCC GTGAA GATC 5' (SEQ ID NO: 21) (bold=SEQ ID NO: 22)
D020 oligonucleotide:
  5' CCAA CTCCA TCACT AGGGG TTCCT 3' (SEQ ID NO: 23) (bold=SEQ ID NO: 24)
  3' GGTT GAGGT AGTGA TCCCC AAGGA GATC 5' (SEQ ID NO: 25) (bold=SEQ ID NO: 26)

The D-5, D-10, D-15 and D-20 oligonucleotide sequences were each inserted between the Xba I and Bal I sites of plasmid pXS-22, which is described in Wang, *J. Mol. Biol.* 250 (1995) 573–580 and *J. Virol.* 70 (1996) 1668–1677. The resulting four plasmids were named pXS-64D-5, pXS-64D-10, pXS-64D-15 and pXS-64D-20 respectively. The blunted ClaI-PvuII fragments from pXS-64D-5, pXS-64D-10, pXS-64D-15 and pXS-64D-20 were then excised and ligated between the ClaI and XbaI sites of these plasmids to generate plasmids pD-5, pD-10, pD-15 and pD-20 respectively containing the D-5, D-10, D-15 and D-20 oligonucleotide sequences in place of the S sequences in both ITRs.

Each of the four foregoing recombinant AAV vectors, pD-5, pD-10, pD-15 and pD-20 may be employed in the methods of the invention. We have determined that to optimize packaging, 10 of the native D-nucleotides are sufficient. The most preferred native 10 D-nucleotides are those included in the pD-10 vector and indicated in bold in the D-10 oligonucleotide sequence above. The pD-15 and pD-20 vectors, or their respective indicated oligonucleotides (see above), may be used but they contain extra, unnecessary nucleotides that would advantageously be eliminated in order to allow for more space in the AAV vector for nucleotides encoding the desired therapeutic molecule. The pD-5 vector works, but with less efficiency. Consequently, the absolute minimal necessary sequence is the 5 nucleotide sequence enumerated in bold in the D-5 oligonucleotide sequence above and contained in the pD-5 vector. The pD-10 vector allows for the insertion of an additional 106 nucleotides.

Nucleic acid sequences encoding therapeutic molecules can be ligated between the ITRs of these vectors using known techniques. The vectors or virions may be formulated into pharmaceutical compositions for administration in human or other mammalian patients.

Plasmid pXS-22 was deposited on Sep. 10, 1996 with the 10801 University Blvd. Manassas, Va. 20110–2209 USA under the terms of the Budapest Treaty on the International Recognition of the Deposit of Microorganisms for Purposes of Patent Procedure. The Accession Number is 97710. An AAV vector, "D10-Kan-FGF2-Sc", which is based upon the vector "pD10", was deposited with the ATCC on Mar. 16, 2000 in accordance with the terms of the Budapest Treaty and was assigned Patent Deposit Designation number PTA-1498. These deposit assures maintenance of a viable culture for 30 years from the date of deposit. The organism(s) deposited will be made available by the ATCC under the terms of the Budapest Treaty, and subject to an agreement between applicant and the ATCC that assures unrestricted availability upon issuance of the pertinent U.S. patent. This deposit is provided as convenience to those of skill in the art, and is not an admission that a deposit is required under 35 U.S.C. 112. The nucleic acid sequence of this deposit, as well as the amino acid sequence of the polypeptide(s) encoded thereby, are incorporated herein by reference and should be referred to in the event of an error in the sequence described herein. A license may be required to make, use, or sell the deposited materials, and no such license is granted hereby.

All patents, patent publications, patent applications and scientific articles mentioned in this specification are herein incorporated by reference. The invention now being fully described, it will be apparent to one of ordinary skill in the art that many changes and modifications can be made thereto without departing from the spirit or scope of the appended claims.

What is claimed is:

1. A recombinant adeno-associated viral (AAV) vector comprising two inverted terminal repeats (ITRs) each of which comprises a D-sequence comprising i) the nucleic acid sequence 5' CTCCA 3' (SEQ ID NO: 12), and ii) a deletion or substitution.

2. The recombinant AAV vector of claim 1, wherein the vector is pD-5.

3. A recombinant adeno-associated viral (AAV) vector comprising two inverted terminal repeats (ITRs) each of which comprises a D-sequence comprising i) the nucleic acid sequence 5' CTCCATCACT 3' (SEQ ID NO: 16), and ii) a deletion or substitution.

4. The recombinant AAV vector of claim 3, wherein the vector is pD-10.

5. A recombinant adeno-associated viral (AAV) vector comprising two inverted terminal repeats (ITRs) each of which comprises a D-sequence comprising i) the nucleic acid sequence 5' CTCCATCACTAGGGG 3' (SEQ ID NO: 20), and ii) a deletion or substitution.

6. The recombinant AAV vector of claim 5, wherein the vector is pD-15.

* * * * *